(12) United States Patent
Swanson, Sr.

(10) Patent No.: US 7,288,118 B1
(45) Date of Patent: Oct. 30, 2007

(54) QUADRICEPS CONTROL DEVICE FOR PROSTHETICS/ORTHOTICS

(75) Inventor: Verner M. Swanson, Sr., Temperance, MI (US)

(73) Assignee: Bionix Prosthetic Solutions, Inc., Toledo, OH (US)

( * ) Notice: Subject to any disclaimer, the term of this patent is extended or adjusted under 35 U.S.C. 154(b) by 0 days.

(21) Appl. No.: 11/041,683

(22) Filed: Jan. 24, 2005

Related U.S. Application Data

(60) Provisional application No. 60/538,681, filed on Jan. 23, 2004.

(51) Int. Cl.
*A61F 2/64* (2006.01)
*A61F 2/68* (2006.01)
(52) U.S. Cl. .............................. 623/46; 623/27; 623/32
(58) Field of Classification Search ............ 623/27–46; 602/26
See application file for complete search history.

(56) References Cited

U.S. PATENT DOCUMENTS

| | | | | |
|---|---|---|---|---|
| 1,316,347 | A * | 9/1919 | Bidou | 623/46 |
| 2,210,269 | A * | 8/1940 | Taylor | 601/33 |
| 4,215,441 | A * | 8/1980 | Wilson | 623/31 |
| 5,016,621 | A * | 5/1991 | Bender | 602/26 |
| 2004/0073149 | A1 * | 4/2004 | Okediji | 602/23 |

* cited by examiner

*Primary Examiner*—Bruce Snow
(74) *Attorney, Agent, or Firm*—Marshall & Melhorn, LLC

(57) ABSTRACT

A quadriceps control device comprises an elongated, elastic member having a first end affixed at an anterior position above the knee and a second end affixed at an anterior position below the knee of the user. The quadriceps control device may be utilized with a prosthetic or orthotic leg assembly. The quadriceps control device mimics to some degree the quadriceps muscle group in human anatomy, to thereby enhance the ability of a user of a prosthetic or orthotic leg assembly to control knee extension and flexion.

10 Claims, 6 Drawing Sheets

QUADRICEPS CONTROL DEVICE FOR PROSTHETICS/ORTHOTICS

RELATED APPLICATION

This application is claiming the benefit, under 35 U.S.C. § 119(e), of the provisional application filed Jan. 23, 2004 under 35 U.S.C. § 111(b), which was granted Ser. No. 60/538,681. This provisional application is hereby incorporated by reference.

BACKGROUND OF THE INVENTION

The invention relates to prosthetic devices and, in particular, to a quadriceps control device for a prosthetic leg assembly. The invention may also be adapted for use with orthotics.

The quadriceps muscles are the large powerful muscles that produce approximately 80% of the total extension power of the human knee. The quadriceps muscles unite to form a strong tendon that attaches under the patella or kneecap. This is one of the reasons why it is so difficult for amputees having amputations above the knee. The loss of the knee joint also results in the loss of the lower attachment of the quadriceps muscle group that is utilized to extend the knee. The hamstring muscles are the knee flexor group; that is, these muscles flex the human knee. However, the quadriceps muscles also control knee flexion by a lengthening or eccentric muscle contracture.

Many users of prosthetic leg assemblies, both above and below the knee, as well as many of those requiring the use of an orthotic leg assembly, encounter difficulties controlling knee extension and flexion due, for example, to muscle weakness, nerve damage, or debilitating disease. Thus, it would be advantageous to provide a device that could to some degree mimic the quadriceps muscle group in human anatomy, to thereby enhance the ability of a user of a prosthetic or orthotic leg assembly to control knee extension and flexion.

BRIEF SUMMARY OF THE INVENTION

The invention relates to prosthetic devices and, in particular, to a quadriceps control device for a prosthetic leg assembly. The quadriceps control device of the invention may be employed with an above the knee prosthetic leg assembly, used herein to refer to any above the knee prosthetic, including a knee disarticulation, above the knee amputation of any length, and hip disarticulation. The quadriceps control device of the invention may also be employed with a below the knee prosthetic leg assembly of any length. The term knee is used herein to refer to a prosthetic or anatomical knee, unless one or the other is specified. The invention may further be adapted for use with orthotics.

The prosthetic or orthotic leg assembly comprises a first support structure positioned above an axis of rotation of a knee, a second support structure positioned below the axis of rotation of the knee, and the quadriceps control device. The quadriceps control device comprises an elongated, elastic member extending along an anterior portion of the assembly, and having a first end affixed to the first support structure and a second end affixed to the second support structure.

The quadriceps control device mimics to some degree the quadriceps muscle group in human anatomy, to thereby enhance the ability of a user of a prosthetic or orthotic leg assembly to control knee extension and flexion. The quadriceps control device of the invention thus allows knee flexion by stretching out or lengthening like a muscle does through an eccentric or lengthening contracture. The device begins to store energy at the beginning of swing phase when the knee begins to flex. It continues to lengthen and gradually stores more energy until it peaks and then the energy is gradually released to extend the knee. The amount of energy released to extend the knee joint is controlled by factors such as how tight the band is, how thick the band is, how wide the band is, how long the band is and how tight the band is adjusted.

BRIEF DESCRIPTION OF THE DRAWINGS

The advantages of the invention will become readily apparent to those skilled in the art from the following detailed description of a preferred embodiment when considered in the light of the accompanying drawings, in which.

DETAILED DESCRIPTION OF THE INVENTION

Figure 1:
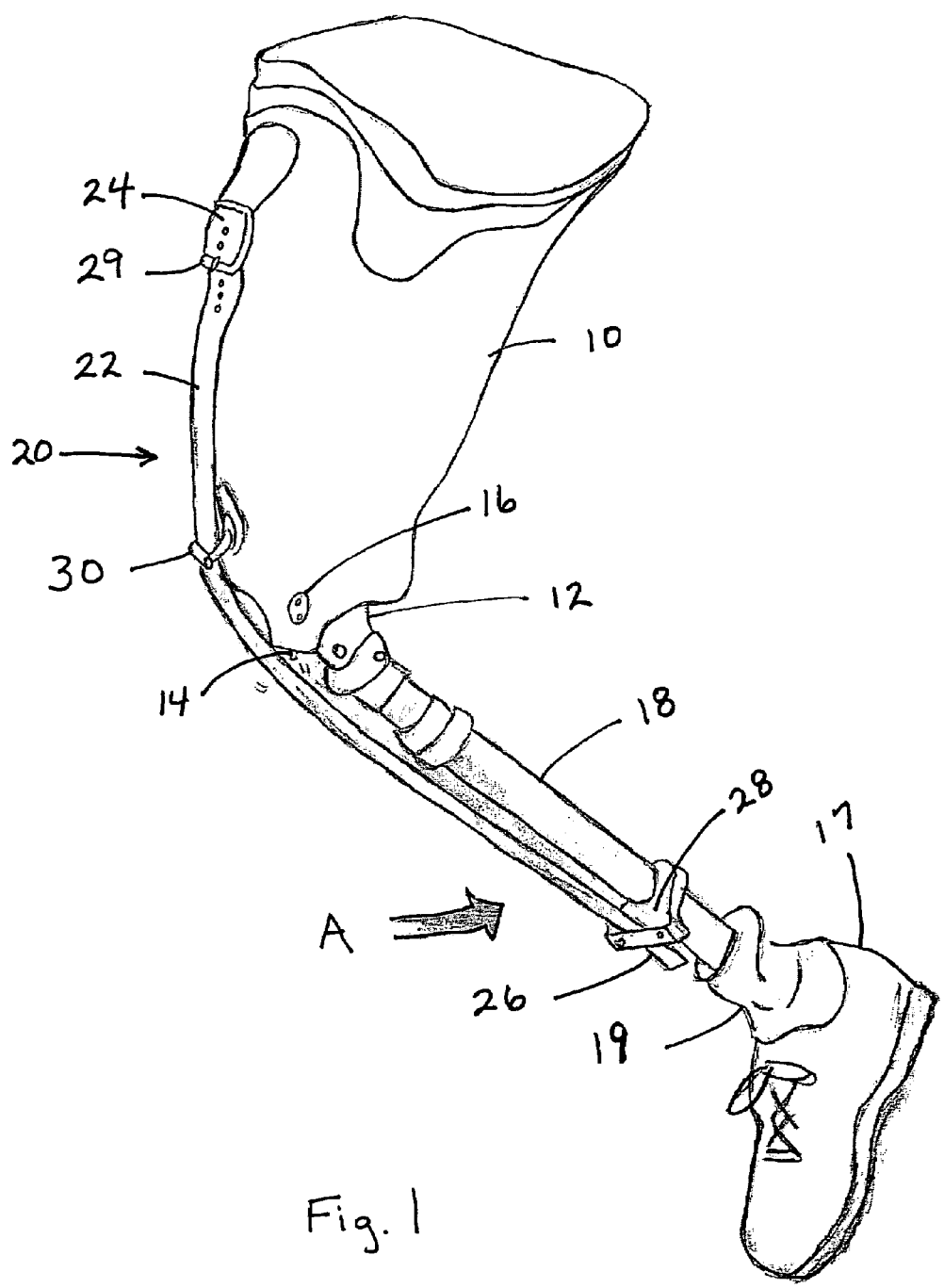
FIG. 1 is a somewhat schematic perspective view of an above the knee prosthetic leg assembly incorporating the quadriceps control device of the invention, the leg being in a position of flexure in the direction of the arrow A.
Figure 2:
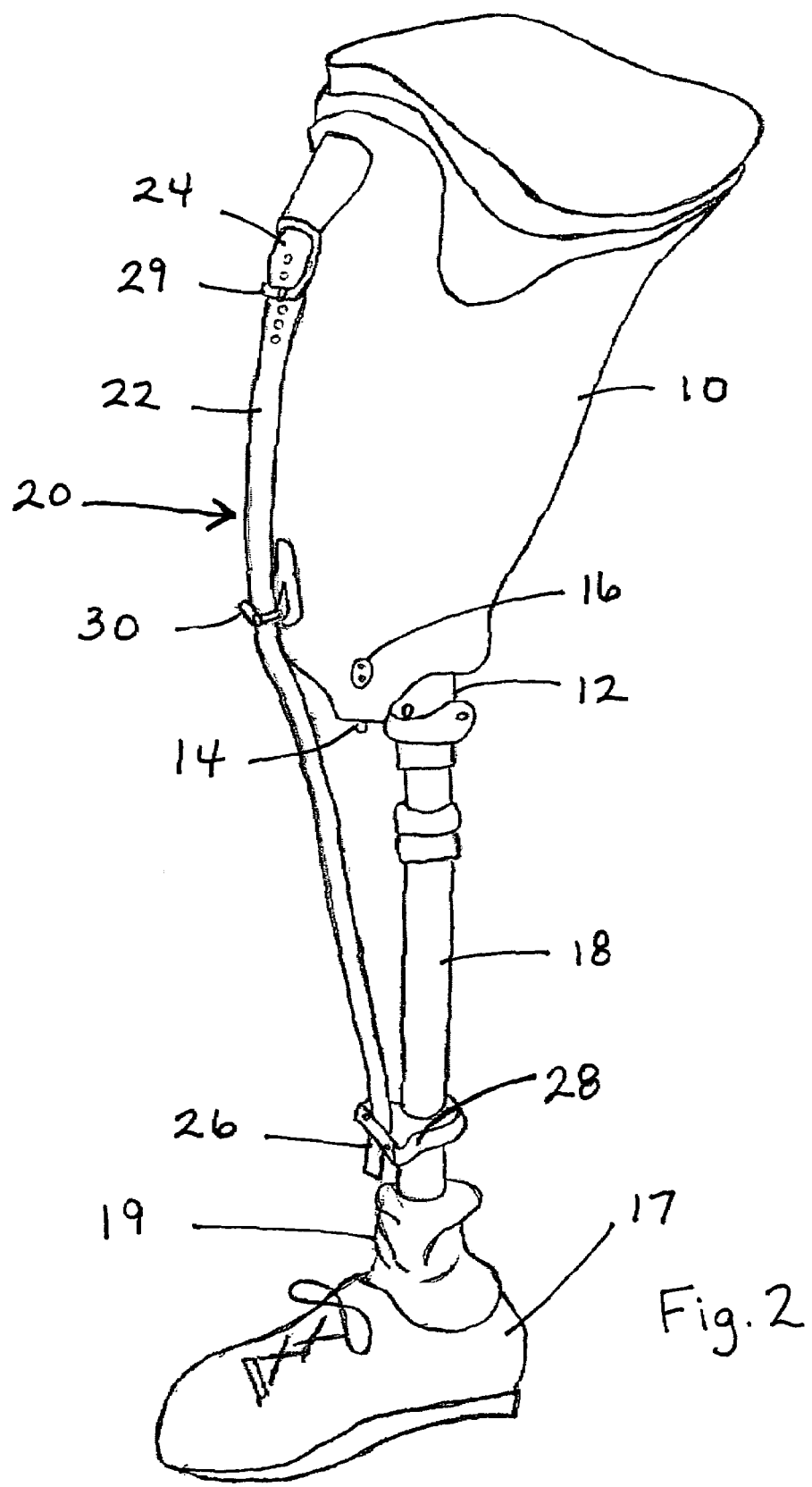
FIG. 2 is a somewhat schematic perspective view of an above the knee-prosthetic leg assembly incorporating the quadriceps control device of the invention, the leg being in a position of complete extension.

Referring now to the drawings, FIGS. 1 and 2 illustrate a residual limb transfemoral socket 10 connected, typically via a lock mechanism, to a prosthetic knee joint 12. Such a transfemoral prosthetic limb is conventionally secured to an amputee's residual limb stump by securing the prosthetic limb to the rigid socket 10. This may be done using suction, harnesses, etc. or combinations thereof. It is commonly done through the use of a locking pin 14. In this technique, the amputee first dons a sock-like liner (not shown) formed of an elastomer and may include fabric cover. The lower or distal end of the liner is formed of a rigid material, such as urethane, and the locking pin extends from this rigid bottom. These liners are well known in the art. The pin 14 is extended through the wall of the socket 10 and a distal adapter mounted within or outside of the socket, and can be locked onto a prosthetic lock mounted to the prosthetic limb to secure the prosthesis. Typically, the lock pin can be released only by moving a pinion gear in a direction parallel to its rotational axis until it disengages from the lock pin, e.g., via a manual release button 16.

In the illustrated embodiment of FIGS. 1 and 2, the prosthesis includes a pylon 18 secured to the knee joint 12. The quadriceps control device of the invention may be used in conjunction with any of the conventional prosthetic knees. The pylon 18 would in turn be connected to an artificial foot 17 by means of an ankle assembly 19, in the conventional manner.

In accordance with the invention, the prosthetic leg assembly is provided with a quadriceps control device, denoted generally by numeral 20 in FIGS. 1 and 2. The quadriceps control device 20 includes an elongated, elastic member 22. As illustrated in FIGS. 1 and 2, the member 22 has a first end 24 affixed to the prosthetic leg assembly at an anterior position above the axis of rotation of the prosthetic knee 12, preferably to the socket 10. As an alternative, the first end 24 of the member 22 could be affixed to an upper portion of the knee 12. The first end 24 of the member 22 could also be affixed to an adapter connected to or part of the socket above the knee frame. The first end 24 of the member 22 may be affixed to the socket 10 by any suitable means, such as mechanical fasteners of any type or adhesives.

As further illustrated in FIGS. 1 and 2, the member 22 has a second end 26 affixed to the prosthetic leg assembly at an anterior position below the axis of rotation of the prosthetic knee 12, so that the member 22 extends over the knee cap cover. The second end 26 of the member 22 is preferably affixed to the pylon 18. However, the second end 26 of the member 22 could also be affixed to a lower portion of the knee 12 or to another lower component of the leg assembly. The second end 26 of the member 22 may be affixed to the pylon 18 by any suitable means, such as mechanical fasteners of any type or adhesives. In the preferred embodiment illustrated in FIGS. 1 and 2, the second end 26 of the member 22 is affixed to the pylon 18 by a means 28 which provides for ready adjustment of the attachment point along the length of the member 22, thereby providing adjustability for the amount of tension applied to the elastic member 22. Adjustment means may also be provided for the point at which the first end 24 of the member 22 is affixed, or for both ends of the member 22. Thus, as illustrated in FIGS. 1 and 2, the first end 24 of the member 22 is affixed to the socket 10 by an adjustable attachment means. Any known means of adjustment may be utilized, such as the belt-like attachment 29 illustrated in FIG. 1.

It may further be preferred to affix the first, second or both ends of the member 20 to the leg assembly in a manner such that the point of attachment is adjustable along the length of the leg assembly. As illustrated, the attachment means 28 may be secured at varying points along the length of the pylon 18, thereby adjusting the length of the member 20 between the points of attachment of the first and second ends thereof.

The ability to adjust the tension in the elongate, elastic member can be advantageous. For example, patients requiring a prosthesis may be debilitated at first and often need to walk with a walker because they do not have the strength or endurance and control of the prosthetic knee. If the quadriceps control device of the invention is tighter (tension on the elastic member is increased), it will resist knee flexion and make the knee more stable. As the patient loosens the tension on the member, it will allow increased knee flexion. As the patient progresses in their rehabilitation, the patient, therapist or prosthetist may loosen the member to fit the patient's needs. It may also be advantageous for the patient to be able to continue to adjust the tension in the member for different activities. For example, if the patient is working in a standing position in one area for a long time, the member may be tightened to resist unwanted knee flexion. Each patient may adjust the elastic member for different vocations, hobbies and sports activities. The patient may adjust the elastic member for slow walking, fast walking, jogging, going up and down steps, ramps, ladders, running, golfing, bowling and other various activities and sports.

While not necessary, it is often useful to provide one or more guides for the member 22, such as the guide 30. During use, the guide 30 prevents undue lateral movement of the member 22 while permitting relative movement between the guide 30 and the member 22 in the direction of the length of the member 22.

The elongate member 22 may be formed of any elastic material of sufficient elasticity and durability. The member 22 is preferably formed of a rubber-like material, such as neoprene. The member 22 may also be formed of various cross-sectional shapes, thicknesses and widths. The member 22 is preferably formed with a rectangular cross-sectional shape with a width significantly greater than its thickness, so that it lies relatively flat against the components of the prosthetic leg assembly. It has further been found to be advantageous to provide the member with a layer of material having reduced friction relative to the remainder of the material, the layer being provided at least in the area of, and facing, the knee. The layer is preferably formed of a strong, reduced friction fabric material. A sleeve of such material (not shown) could also be provided about the member in the area of the knee to reduce friction and wear.

In use, the quadriceps control device 20 generally simulates the quadriceps muscle of the user. The prosthetic knee 12 permits movement of the upper part of the prosthesis with respect to its lower part, about an axis of rotation, analogous to the movement of the femur with respect to the tibia about the articulation of the human knee. This movement is between a position of complete extension (where the leg is straight, as shown in FIG. 2) and a position of flexure (where the leg is bent, as shown in FIG. 1). As the prosthetic leg assembly is moved during locomotion from a position of complete extension to a position of flexure in the direction of the arrow A of FIG. 1, the member 22 is stretched about the front of the knee 12, increasing the tension on the member 22.

When the leg assembly is then moved from a position of flexure back to a position of extension, in a direction opposite to the arrow A of FIG. 1, the energy stored in the elastic member 22 is released. The farther the attachment points of the first and second ends 24, 26 of the member 22 are from the knee 12, the more energy is stored during flexure and then released during extension of the leg assembly.

The member 22 thereby aids the user with extension of the knee. As a result, the user can experience significant increases in ease of walking and running. The benefit is especially significant at higher speeds. The invention enhances knee stability by allowing tightening of the member 22. An increase in tension in the member 22 creates more stability, while a decrease in tension creates less stability. The invention also enhances general control and timing of the knee throughout the swing phase by allowing adjustment of the tension in the member 22.

Figure 3:
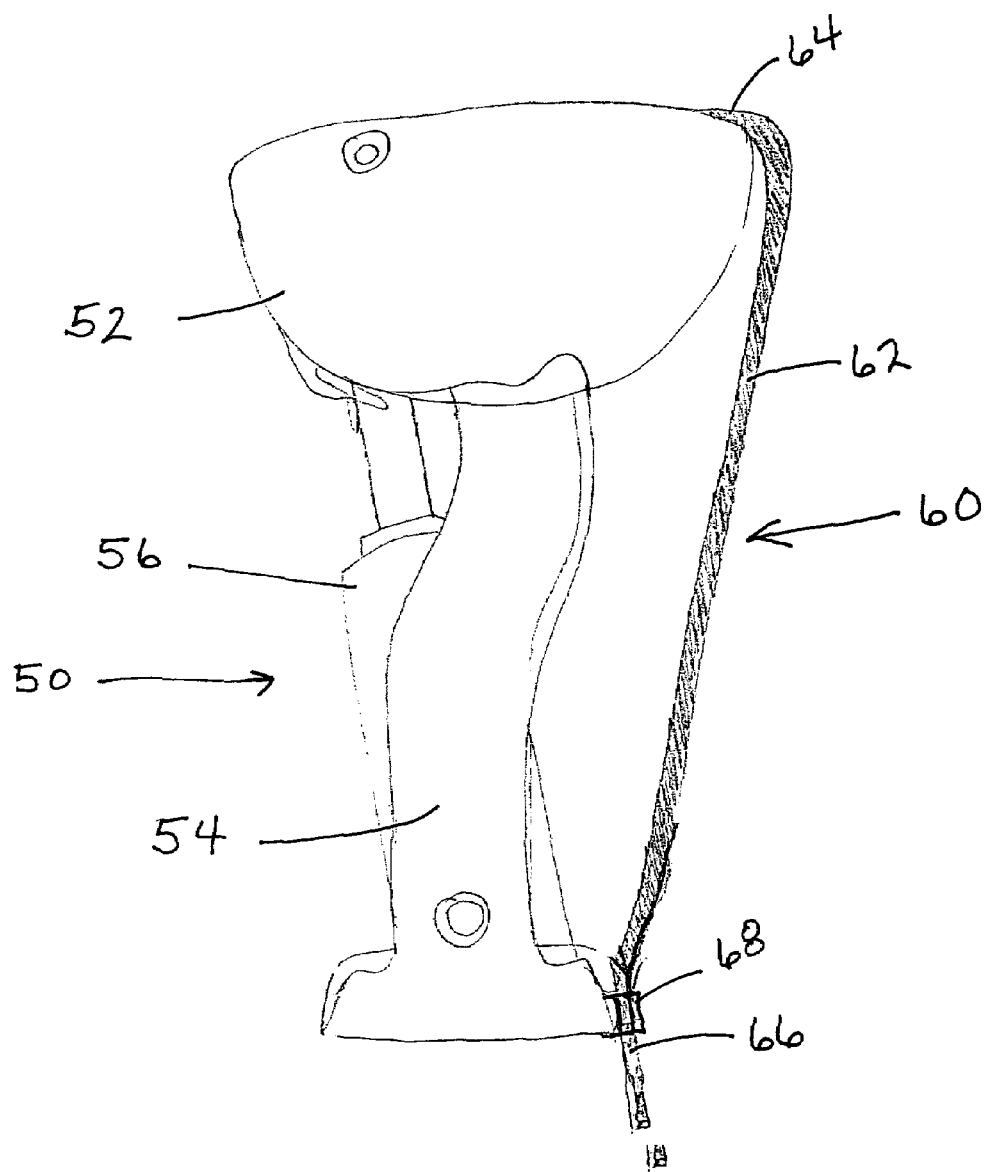
FIG. 3 is a somewhat schematic side view of an alternate embodiment of a prosthetic knee incorporating the quadriceps control device of the invention, the knee being in a position of complete extension.

Referring to FIG. 3, an alternate embodiment of the invention is illustrated. FIG. 3 shows a prosthetic knee assembly 50 having a knee cap 52 adapted to be secured to a residual limb transfemoral socket (not shown). A knee frame member 54 extends downward from the knee cap 52 and supports a hydraulic cylinder 56 in the conventional manner. The hydraulic cylinder 56 helps to control the relative movement of the upper part of the prosthetic device (supporting the socket) with respect to its lower part (connected to the leg), as is known.

The prosthetic knee assembly 50 is provided with a quadriceps control device, denoted generally by numeral 60 in FIG. 3. The quadriceps control device 60 includes an elongated, elastic member 62. The member 62 has a first end 64 affixed to an upper portion of the knee cap 52 at an anterior position. The first end 64 of the member 62 may be affixed to the knee cap 52 by any suitable means, such as mechanical fasteners of any type or adhesives.

As further illustrated in FIG. 3, the member 62 has a second end 66 affixed to the knee frame 54 at an anterior position below the axis of rotation of the knee. The second end 66 of the member 62 may be affixed to the knee frame 54 by any suitable means, such as mechanical fasteners of any type or adhesives. In the preferred embodiment illustrated, the second end 66 of the member 62 is affixed to the knee frame 54 by a means 68 which provides for ready adjustment of the attachment point along the length of the member 62, thereby providing adjustability for the amount of tension applied to the elastic member 62. Adjustment means may be provided for the point at which the first end 64 of the member 62 is affixed, or at both ends of the member 62. Any known means of adjustment may be utilized, such as a belt-like attachment.

The member 62 may be formed of any elastic material of sufficient elasticity and durability. The member 62 is preferably formed of a rubber-like material, such as neoprene. The member 62 may also be formed of various cross-sectional shapes, thicknesses and widths. The member 62 is preferably formed with a rectangular cross-sectional shape with a width significantly greater than its thickness, so that it lies relatively flat against the components of the prosthetic knee assembly.

The extension aid 60 operates in a similar manner to the embodiment shown in FIGS. 1 and 2. When the leg assembly is then moved from a position of flexure back to a position of extension, the energy stored in the elastic member 62 is released. The member 62 thereby aids the user with extension of the knee.

Figure 4:
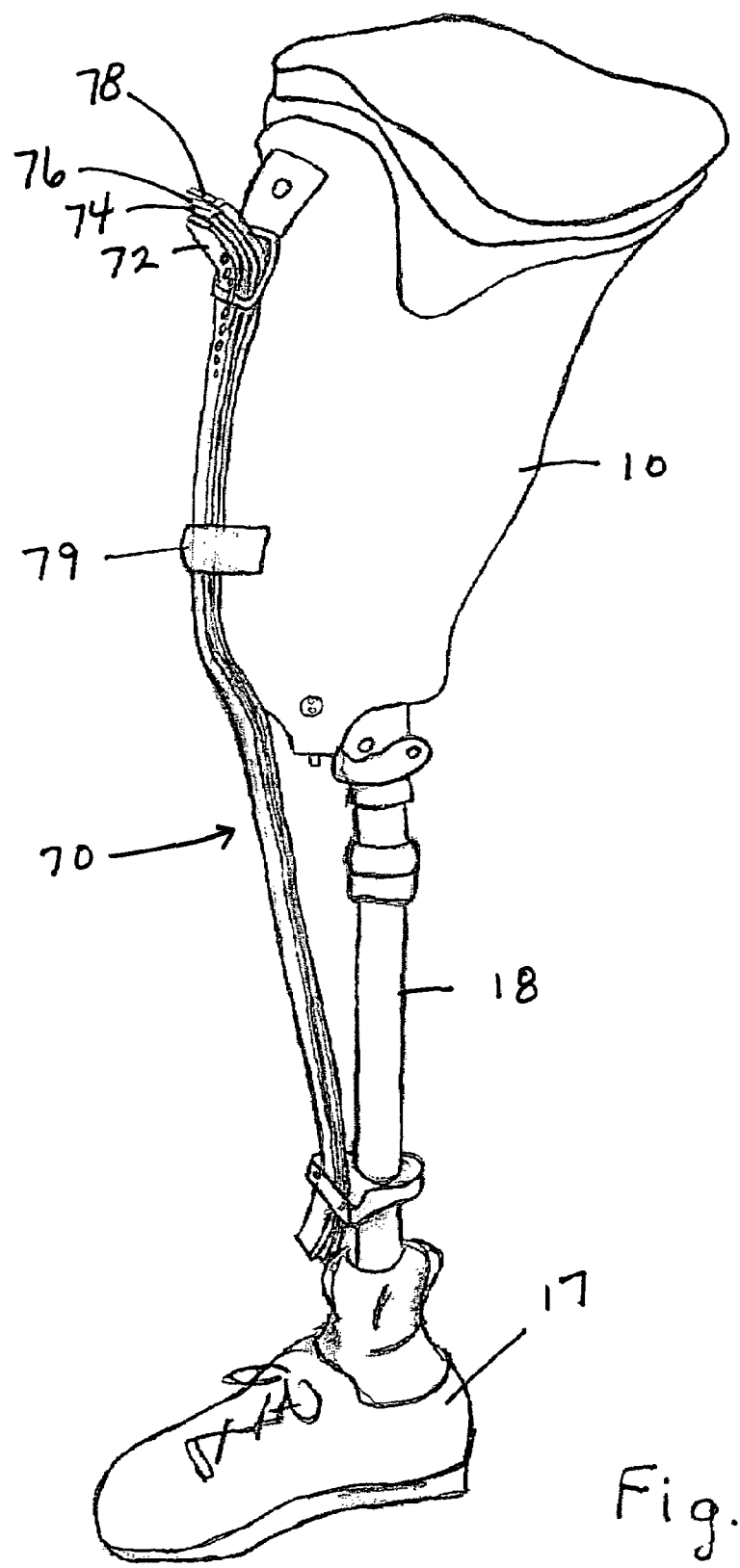
FIG. 4 is a somewhat schematic perspective view of a further embodiment of the quadriceps control device of the invention.

Referring now to FIG. 4, a further embodiment of the quadriceps control device of the invention is illustrated. In this embodiment, the quadriceps control device 70 comprises a plurality of elongated, elastic members 72, 74, 76 and 78. Each of these members is secured in the manner described above for the other embodiments. These members all have a first end affixed to the prosthetic leg assembly above the knee and second ends affixed below the knee. The members may all have their lateral movement restrained by guide 79. The members are preferably adjustable, and it may be preferable to adjust members so that different levels of tension are provided in various ones of the members.

The members 72, 74, 76 and 78 may be formed of any elastic material of sufficient elasticity and durability. The members are preferably formed of a rubber-like material, such as neoprene, but it may be advantages to form the various members of different materials. The members may also be formed of various cross-sectional shapes, thicknesses and widths, and it may be advantageous to form different members with different cross-sectional shapes, thicknesses and widths. The members are preferably formed with a rectangular cross-sectional shape with a width significantly greater than its thickness, so that they lie relatively flat. The various members may be arranged one relative to the others in various ways, but are preferably arranged to lie one over top of the other.

Figure 5:
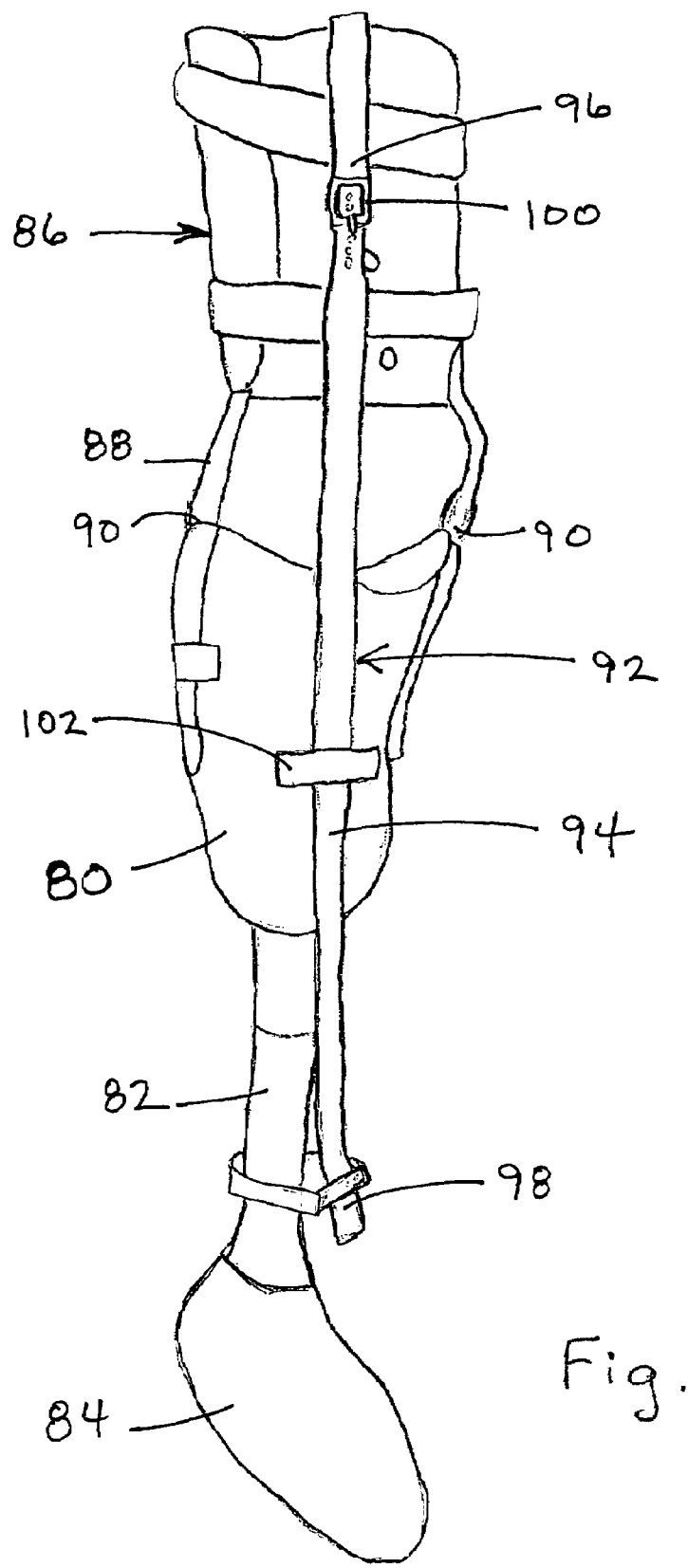
FIG. 5 is a somewhat schematic perspective view of a below the knee prosthetic leg assembly incorporating the quadriceps control device of the invention, the leg being in a position of complete extension.

In another embodiment, illustrated in FIG. 5, a quadriceps control device is used in connection with a below the knee prosthetic leg assembly. As illustrated, a residual limb transtibial socket 80 is connected to a pylon 82 that is in turn connected to an artificial foot 84 in the conventional manner. The transtibial socket 80 is connected to a thigh corset 86 by a metal frame structure 88 having a pair of hinges 90 intended to generally align with the axis of rotation of the user's anatomical knee.

In this application, a quadriceps control device 92 is provided that includes an elongated, elastic member 94 attached to the assembly; a first end 96 attached above the knee to the thigh corset 86 and a second end 98 attached below the knee. The member 94 is preferably adjustable as to the amount of tension applied thereto, for instance by the belt-type fastener 100 shown. A guide 102 affixed to the socket 80 operates as in the other embodiments to prevent undue lateral movement of the member 94. The invention would thus enhance and facilitate the wearer of the below the knee prosthetic leg assembly with knee extension.

Figure 6:
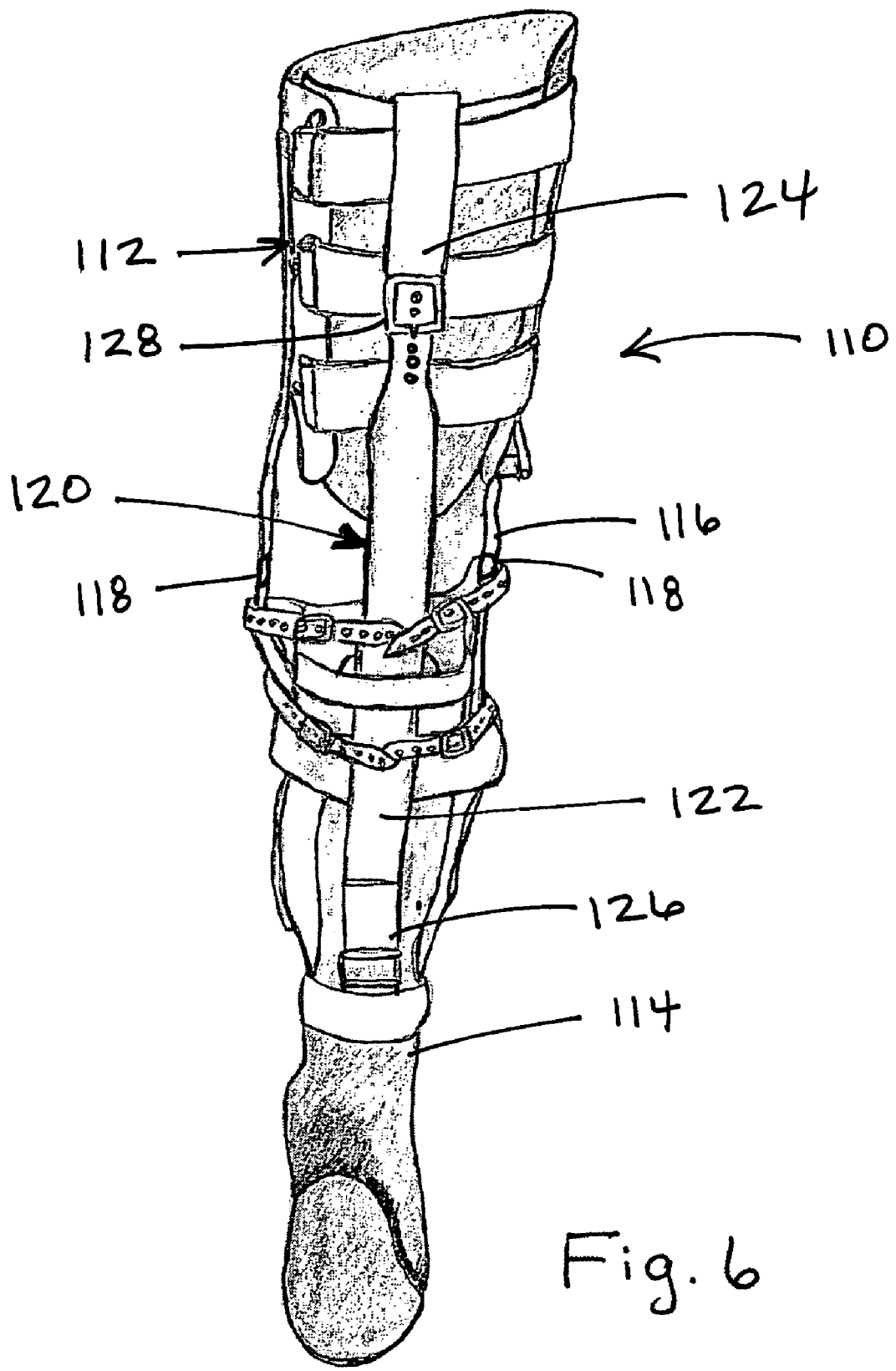
FIG. 6 is a somewhat schematic front view of an orthotic leg assembly incorporating the quadriceps control device of the invention, the leg being in a position of complete extension.

In a further embodiment, illustrated in FIG. 6, the invention is applied to an orthotic, such as the plastic and metal knee brace illustrated and denoted generally by the numeral 110. As shown, the orthotic leg assembly 110 includes a thigh corset 112 and a rigid plastic lower limb brace 114, typically interconnected by a metal frame structure 116 having a pair of hinges 118 intended to generally align with the axis of rotation of the user's anatomical knee.

In this application, the quadriceps control device 120 again includes an elongated, elastic member 122 attached to the orthotic; a first end 124 attached above the knee to the thigh corset 112 and a second end 126 attached below the knee. The member 112 is preferably be adjustable as to the amount of tension applied thereto, for instance by the belt-type fastener 128 shown. The invention would thus enhance and facilitate the wearer of the orthotic with knee extension in cases of, as examples, muscle weakness, nerve damage, or debilitating diseases.

In accordance with the provisions of the patent statutes, the invention has been described in what is considered to represent its preferred embodiments. However, it should be noted that the invention could be practiced otherwise than as specifically illustrated and described without departing from its spirit or scope.

What is claimed is:

1. A prosthetic leg assembly comprising a prosthetic knee joint having an axis of rotation, a residual limb transfemoral socket connected to the prosthetic knee joint above the axis of rotation, a lower leg support structure connected to the prosthetic knee joint below the axis of rotation, and a quadriceps control device, the quadriceps control device comprising an elongated, elastic member having a width significantly greater than its thickness, so that it lies relatively flat against the prosthetic leg assembly, the elastic member having a first end affixed to the socket and a second end affixed to the lower leg support structure, the member extending along the prosthetic leg assembly from an anterior position above the axis of rotation of the prosthetic knee joint to an anterior position below the axis of rotation of the prosthetic knee joint.

2. The assembly of claim 1, wherein the first, second or both ends of the member is affixed to the leg assembly by an attachment structure which provides for adjustment of the point along the length of the member at which the member is affixed to the leg assembly, thereby providing adjustability for the amount of tension applied to the member.

3. The assembly of claim 1, wherein the attachment structure is a belt-like attachment.

4. The assembly of claim 1, wherein the member has a rectangular cross-sectional shape.

5. The assembly of claim 1, further comprising a pylon, wherein the second end of the member is affixed to the pylon.

6. The assembly of claim 1, comprising a plurality of elongated, elastic members, each having a first end affixed to the socket and a second end affixed to the lower leg support structure.

7. The assembly of claim 6, wherein one or more of the plurality of members is arranged to lie over one or more of the other of the plurality of members.

8. The assembly of claim 6, wherein the plurality of members are attached in a manner such that the amount of tension in one or more of the members differs from the amount of tension in one or more of the others of the members.

9. The assembly of claim 1, further comprising a guide in contact with the member between the first and second ends thereof, the guide limiting lateral movement of the member.

10. The assembly of claim 1, wherein at least a portion of the member is provided with a layer of material having reduced friction relative to the remainder of the member.

* * * * *